United States Patent [19]

Smith

[11] 4,137,270
[45] Jan. 30, 1979

[54] 2-DECARBOXY-2-HYDROXYMETHYL-13,14-DIDEHYDRO-ω-ARYL-PG COMPOUNDS

[75] Inventor: Herman W. Smith, Kalamazoo, Mich.

[73] Assignee: The Upjohn Company, Kalamazoo, Mich.

[21] Appl. No.: 814,410

[22] Filed: Jul. 11, 1977

Related U.S. Application Data

[62] Division of Ser. No. 708,752, Jul. 26, 1976, Pat. No. 4,058,564.

[51] Int. Cl.$^2$ ............................................. C07C 49/76
[52] U.S. Cl. .................................................. 260/590 C
[58] Field of Search .......................... 260/590 C, 514 D

[56] References Cited

U.S. PATENT DOCUMENTS

| 3,932,496 | 1/1976 | Jung | 260/514 D |
|---|---|---|---|
| 3,935,254 | 1/1976 | Gandolfe et al. | 260/514 D |
| 3,984,400 | 10/1976 | Eggles et al. | 260/468 D |

*Primary Examiner*—James O. Thomas, Jr.
*Assistant Examiner*—James H. Reamer
*Attorney, Agent, or Firm*—Robert A. Armitage

[57] ABSTRACT

This invention comprises certain analogs of the prostaglandins in which the C-1 carboxyl is replaced by a primary alcohol and the double bond between C-13 and C-14 is replaced by a triple bond. Also provided in this invention, are novel chemical processes useful in the preparation of the above prostaglandin analogs. These prostaglandin analogs exhibit prostaglandin-like activity, and are accordingly useful for the same pharmacological purposes as the prostaglandins. Among these purposes are blood pressure lowering, labor induction at term, reproductive-cycle regulation, gastric antisecretory action, and the like.

68 Claims, No Drawings

2-DECARBOXY-2-HYDROXYMETHYL-13,14-DIDEHYDRO-ω-ARYL-PG COMPOUNDS

The present application is a divisional application of Ser. No. 708,752, filed July 26, 1976, now issued as U.S. Pat. No. 4,058,564 on Nov. 15, 1977.

The present invention relates to prostaglandin analogs for which the essential material constituting a disclosure therefor is incorporated by reference here from U.S. Pat. No. 4,058,564, issued Nov. 15, 1977.

I claim:

1. A prostaglandin analog of the formula

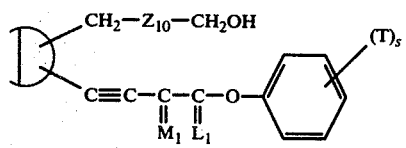

wherein D is

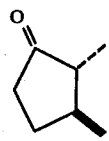,

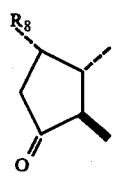,

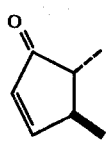

or

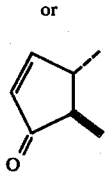

wherein $R_8$ is hydrogen or hydroxy;
wherein $M_1$ is

or

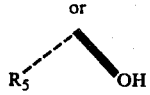

wherein $R_5$ is hydrogen or methyl;
wherein $L_1$ is

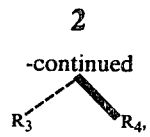, or a mixture of

and

, wherein $R_3$ and $R_4$ are hydrogen or methyl being the same or different;
wherein $Z_{10}$ is
(1) cis-CH=CH—CH—(CH$_2$)$_g$—CH$_2$—
(2) cis-CH=CH—CH$_2$—(CH$_2$)$_g$—CF$_2$—,
(3) cis-CH$_2$—CH=CH—(CH$_2$)$_g$—CH$_2$—,
(4) —(CH$_2$)$_3$—(CH$_2$)$_g$—CH$_2$—,
(5) —(CH$_2$)$_3$—(CH$_2$)$_g$—CF$_2$— or
(6) —CH$_2$—O—CH$_2$—(CH$_2$)$_g$—CH$_2$—,
wherein g is one, 2, or 3; and
wherein s is one to 3, inclusive and T is chloro, fluoro, trifluoromethyl, alkyl of one to 3 carbon atoms, inclusive, or alkoxy of one to 3 carbon atoms, inclusive, the various T's being the same or different, with the proviso that not more than two are other than alkyl, with the further proviso that $Z_3$ is oxa only when $R_3$ and $R_4$ are hydrogen or methyl, being the same or different.

2. A prostaglandin analog according to claim 1, wherein D is

3. A prostaglandin analog according to claim 2, wherein $R_8$ is hydrogen.

4. A prostaglandin analog according to claim 2, wherein $R_8$ is hydroxy.

5. A prostaglandin analog according to claim 1, wherein D is

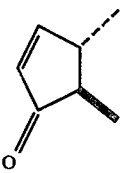

6. The prostaglandin analog according to claim 1, wherein D is

7. A prostaglandin analog according to claim 1, wherein is

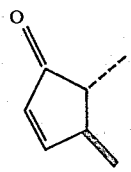

8. A prostaglandin analog according to claim 7, wherein $Z_{10}$ is cis—CH=CH—CH$_2$—(CH$_2$)$_g$—CF$_2$—.

9. 2-Decarboxy-2-hydroxymethyl-2,2-difluoro-13,14-didehydro-16-phenoxy-17,18,19,20-tetranor-PGE$_2$, a prostaglandin analog according to claim 8.

10. A prostaglandin analog according to claim 7, wherein $Z_{10}$ is —(CH$_2$)$_3$—(CH$_2$)$_g$—CF$_2$—.

11. 2-Decarboxy-2-hydroxymethyl-2,2-difluoro-13,14-didehydro-16-phenoxy-17,18,19,20-tetranor-PGE$_1$, a prostaglandin analog according to claim 10.

12. A prostaglandin analog according to claim 7, wherein $Z_{10}$ is cis-CH$_2$—CH=CH—(CH$_2$)$_g$—CH$_2$—.

13. 2-Decarboxy-2-hydroxymethyl-cis-4,5-didehydro-13,14-didehydro-16-phenoxy-17,18,19,20-tetranor-PGE$_1$, a prostaglandin analog according to claim 12.

14. A prostaglandin analog according to claim 7, wherein $Z_{10}$ is —CH$_2$—O—CH$_2$—(CH$_2$)$_g$—CH$_2$—.

15. 2-Decarboxy-2-hydroxymethyl-5-oxa-13,14-didehydro-16-phenoxy-17,18,19,20-tetranor-PGE$_1$, a prostaglandin analog according to claim 14.

16. A prostaglandin analog according to claim 7, wherein $Z_{10}$ is —(CH$_2$)$_3$—(CH$_2$)$_g$—CH$_2$—.

17. A prostaglandin analog according to claim 16, wherein $M_1$ is

18. 2-Decarboxy-2-hydroxymethyl-15-epi-13,14-didehydro-16-phenoxy-17,18,19,20-tetranor-PGE$_1$, a prostaglandin analog according to claim 17.

19. A prostaglandin analog according to claim 16, wherein $M_1$ is

20. A prostaglandin analog according to claim 19, wherein m is 3.

21. A prostaglandin analog according to claim 20, wherein g is 3.

22. 2-Decarboxy-2-hydroxymethyl-2a,2b-dihomo-15-methyl-13,14-didehydro-16-phenoxy-17,18,19,20-tetranor-PGE$_1$, a prostaglandin analog according to claim 21.

23. 2-Decarboxy-2-hydroxymethyl-2a,2b-dihomo-13,14-didehydro-16-phenoxy-17,18,19,20-tetranor-PGE$_1$, a prostaglandin analog according to claim 21.

24. A prostaglandin analog according to claim 20, wherein g is 1.

25. A prostaglandin analog according to claim 24, wherein at least one of $R_3$ and $R_4$ is methyl.

26. A prostaglandin analog according to claim 25 wherein $R_3$ and $R_4$ are both methyl.

27. 2-Decarboxy-2-hydroxymethyl-13,14-didehydro-16-methyl-16-phenoxy-18,19,20-trinor-PGE$_1$, a prostaglandin analog according to claim 26.

28. A prostaglandin analog according to claim 24, wherein at least two of $R_3$, $R_4$, and $R_5$ are methyl.

29. A prostaglandin analog according to claim 28, wherein $R_3$, $R_4$, and $R_5$ are all methyl.

30. 2-Decarboxy-2-hydroxymethyl-15,16-dimethyl-13,14-didehyro-16-phenoxy-18,19,20-trinor-PGE$_1$, a prostaglandin analog according to claim 29.

31. A prostaglandin analog according to claim 24, wherein $R_3$ and $R_4$ are both hydrogen.

32. A prostaglandin analog according to claim 31, wherein $R_5$ is methyl.

33. 2-Decarboxy-2-hydroxymethyl-15-methyl-13,14-didehydro-16-phenoxy-17,18,19,20-tetranor-PGE$_1$, a prostaglandin analog according to claim 32.

34. A prostaglandin analog according to claim 31, wherein $R_5$ is hydrogen.

35. 2-Decarboxy-2-hydroxymethyl-13,14-didehydro-16-phenoxy-17,18,19,20-tetranor-PGE$_1$, a prostaglandin analog according to claim 34.

36. A prostaglandin analog according to claim 7, wherein $Z_{10}$ is cis-CH=CH—CH$_2$—(CH$_2$)$_g$—CH$_2$.

37. A prostaglandin analog according to claim 36, wherein $M_1$ is

38. A prostaglandin analog according to claim 37, wherein m is 3.

39. A prostaglandin analog according to claim 38, wherein g is 3.

40. 2-Decarboxy-2-hydroxymethyl-2a,2b-dihomo-15-epi-15-methyl-13,14-didehydro-16-phenoxy-17,18,19,20-tetranor-PGE$_2$, a prostaglandin analog according to claim 39.

41. 2-Decarboxy-2-hydroxymethyl-2a,2b-dihomo-15-epi-13,14-didehydro-16-phenoxy-17,18,19,20-tetranor-PGE$_2$, a prostaglandin analog according to claim 39.

42. A prostaglandin analog according to claim 38, wherein g is 1.

43. A prostaglandin analog according to claim 42, wherein at least one of $R_3$ and $R_4$ is methyl.

44. 2-Decarboxy-2-hydroxymethyl-15-epi-13,14-didehydro-16-methyl-16-phenoxy-18,19,20-trinor-PGE$_2$, a prostaglandin analog according to claim 43.

45. A prostaglandin analog according to claim 42, wherein at least two of $R_3$, $R_4$, and $R_5$ are methyl.

46. 2-Decarboxy-2-hydroxymethyl-15-epi-15,16-dimethyl-13,14-didehydro-16-phenoxy-18,19,20-trinor-PGE$_2$, a prostaglandin analog according to claim 45.

47. A prostaglandin analog according to claim 42, wherein $R_3$ and $R_4$ are both hydrogen.

48. 2-Decarboxy-2-hydroxymethyl-15-epi-15-methyl-13,14-didehydro-16-phenoxy-17,18,19,20-tetranor-PGE$_2$, a prostaglandin analog according to claim 47.

49. A prostaglandin analog according to claim 36, wherein $M_1$ is

50. A prostaglandin analog according to claim 49, wherein m is 3.
51. A prostaglandin analog according to claim 50, wherein g is 3.
52. A prostaglandin analog according to claim 51, wherein at least one of $R_3$ and $R_4$ is methyl.
53. 2-Decarboxy-2-hydroxymethyl-2a,2b-dihomo-16,16-dimethyl-13,14-didehydro-16-phenoxy-17,18,19,20-tetranor-PGE$_2$, a prostaglandin analog according to claim 52.
54. A prostaglandin analog according to claim 51, wherein at least two of $R_3$, $R_4$, and $R_5$ are methyl.
55. 2-Decarboxy-2-hydroxymethyl-2a,2b-dihomo-15,16-dimethyl-13,14-didehydro-16-phenoxy-18,19,20-trinor-PGE$_2$, a prostaglandin analog according to claim 54.
56. A prostaglandin analog according to claim 51, wherein $R_3$ and $R_4$ are both hydrogen.
57. 2-Decarboxy-2-hydroxymethyl-2a,2b-dihomo-15-methyl-13,14-didehydro-16-phenoxy-17,18,19,20-tetranor-PGE$_2$, a prostaglandin analog according to claim 56.
58. A prostaglandin analog according to claim 50, wherein g is 1.
59. a prostaglandin analog according to claim 58, wherein at least one of $R_3$ and $R_4$ is methyl.
60. A prostaglandin analog according to claim 59, wherein only one of $R_3$ and $R_4$ is methyl.
61. 2-Decarboxy-2-hydroxymethyl-13,14-didehydro-16-phenoxy-18,19,20-trinor-PGE$_2$, a prostaglandin analog according to claim 60.
62. A prostaglandin analog according to claim 59, wherein $R_3$ and $R_4$ are both methyl.
63. 2-Decarboxy-2-hydroxymethyl-13,14-didehydro-16-methyl-16-phenoxy-18,19,20-trinor-PGE$_2$, a prostaglandin analog according to claim 62.
64. A prostaglandin analog according to claim 58, wherein $R_3$ and $R_4$ are both hydrogen.
65. A prostaglandin analog according to claim 64, wherein $R_5$ is methyl.
66. 2-Decarboxy-2-hydroxymethyl-15-methyl-13,14-didehydro-16-phenoxy-17,18,19,20-tetranor-PGE$_2$, a prostaglandin analog according to claim 65.
67. A prostaglandin analog according to claim 64, wherein $R_5$ is hydrogen.
68. 2-Decarboxy-2-hydroxymethyl-13,14-didehydro-16-phenoxy-17,18,19,20-tetranor-PGE$_2$, a prostaglandin analog according to claim 67.

* * * * *

UNITED STATES PATENT OFFICE
CERTIFICATE OF CORRECTION

Patent No. 4,137,270  Dated  30 January 1979

Inventor(s)  Herman W. Smith

It is certified that error appears in the above-identified patent and that said Letters Patent are hereby corrected as shown below:

Column 2, line 20, "cis-CH=CH-CH-$(CH_2)_g$-$CH_2$-" should read -- cis-CH=CH-$CH_2$-$(CH_2)_g$-$CH_2$- --; line 29, "wherein s is one to 3," should read -- wherein s is zero to 3, --;

Column 3, line 10, "wherein is" should read -- wherein $D$ is --; lines 61-62, delete claim 20; line 63, "according to claim 20" should read -- according to claim 19 --;

Column 4, lines 41-42, delete claim 38; line 43, "according to claim 38" should read -- according to claim 37 --;

Column 5, lines 8-9, delete claim 50; line 10, "according to claim 50" should read -- according to claim 49 --.

Signed and Sealed this

Ninth Day of September 1980

[SEAL]

Attest:

SIDNEY A. DIAMOND

Attesting Officer  Commissioner of Patents and Trademarks